United States Patent [19]

O'Brien

[11] Patent Number: 5,124,434
[45] Date of Patent: Jun. 23, 1992

[54] POLYESTERS FOR USE IN BLOOD PARTITIONING COMPOSITIONS

[75] Inventor: William L. O'Brien, Cincinnati, Ohio

[73] Assignee: Henkel Corporation, Ambler, Pa.

[21] Appl. No.: 746,261

[22] Filed: Aug. 15, 1991

Related U.S. Application Data

[63] Continuation-in-part of Ser. No. 595,625, Oct. 5, 1990, abandoned, which is a continuation of Ser. No. 444,917, Dec. 4, 1989, abandoned.

[51] Int. Cl.$^5$ .............................................. C08G 63/16
[52] U.S. Cl. ................... 528/272; 528/295.3; 528/295.5; 528/296; 528/300; 528/302; 528/303; 525/88; 525/111.5; 525/165; 525/168; 525/174
[58] Field of Search ................. 528/272, 295.3, 295.5, 528/296, 300, 302, 303; 525/88, 111.5, 165, 168, 174

[56] References Cited

U.S. PATENT DOCUMENTS

| | | | |
|---|---|---|---|
| 4,101,422 | 7/1978 | Lamont et al. | 210/84 |
| 4,148,764 | 4/1979 | Lamont et al. | 106/253 |
| 4,480,087 | 10/1984 | Trotter et al. | 528/302 |

*Primary Examiner*—John Kight, III
*Assistant Examiner*—Sam A. Acquah
*Attorney, Agent, or Firm*—Ernest G. Szoke; Wayne C. Jaeschke; John E. Drach

[57] ABSTRACT

A polyester is provided which facilitates the separation of blood into light and heavy phases via centrifugation in a blood collection vessel. The polyester is useful as a component of a partitioning composition formulated to have appropriate specific gravity to be positioned intermediate the light and heavy blood phases during centrifugation. A partitioning composition including a polyester of the invention provides a particular advantage in blood collection vessels used in therapeutic drug monitoring, due to the relatively low affinity between the polyester component of the composition and commonly monitored classes of drugs.

10 Claims, No Drawings

POLYESTERS FOR USE IN BLOOD PARTITIONING COMPOSITIONS

CROSS-REFERENCE TO RELATED APPLICATIONS

This application is a continuation-in-part of application Ser. No. 07/595,625 filed on Oct. 5, 1990, abandoned, which is a continuation of application Ser. No. 07/444,917 filed on Dec. 4, 1989.

BACKGROUND OF THE INVENTION

1. Field of the Invention

The present invention relates to polyesters useful for facilitating the separation of blood serum or plasma from the cellular portion of blood.

2. Description of the Related Art

The polyesters of the invention are conveniently formulated into a partitioning composition for use in a blood collection vessel in which the blood sample is subjected to centrifugation until the cellular portion and serum or plasma are completely separated. The physical and chemical properties of the partitioning composition are such that a continuous, integral seal is provided between the separated blood phases, thereby maintaining separation of the phases after centrifugation and simplifying removal of the serum or plasma from the blood collection vessel. The high volume testing of blood components in hospitals and clinics has led to the development of various devices to simplify the collection of blood samples and preparation of the samples for analysis. Typically, whole blood is collected in an evacuated, elongated glass tube that is permanently closed at one end and sealed at the other end by a rubber stopper having a diaphragm which is penetrated by the double-tipped cannula used to draw the patient's blood. After the desired quantity of blood is collected, the collection vessel is subjected to centrifugation to yield two distinct phases comprising the cellular portion of the blood (heavy phase) and the blood serum or plasma (light phase). The light phase is typically removed from the collection vessel, e.g., via pipette or decantation, for testing.

It has been proposed heretofore to provide manufactured, seal-forming members, e.g., resilient pistons, spools, discs and the like, in blood collection vessels to serve as mechanical barriers between the two separated phases. Because of the high cost of manufacturing such devices to the close tolerances required to provide a functional seal, they have been supplanted by fluid sealant compositions. Fluid sealant compositions are formulated to have a specific gravity intermediate the two blood phases sought to be separated, so as to provide a partition at the interface between the cellular and serum phases. Such compositions typically include a polymer base material, one or more additives for adjusting the specific gravity and viscosity of the resultant composition, and optionally, a network former. Representative prior art fluid sealant compositions include: styrene beads coated with an anti-coagulant (U.S. Pat. No. 3,464,890); silicone fluid having silica dispersed therein (U.S. Pat. No. 3,780,935); a homogenous, hydrophobic copolyester including a suitable filler, e.g., silica (U.S. Pat. Nos. 4,101,422 and 4,148,764); a liquid α-olefin-dialkylmaleate, together with an aliphatic amine derivative of smectite clay or powdered silica (U.S. Pat. No. 4,310,430); the reaction product of a silicone fluid with a silica filler and a network former (U.S. Pat. No. 4,386,003); and a mixture of compatible viscous liquids, e.g., epoxidized vegetable oil and chlorinated polybutene, and a thixotropy-imparting agent, e.g., powdered silica (U.S. Pat. No. 4,534,798).

Ideally, a commercially useful blood partitioning composition should maintain uniform physical and chemical properties for extended time periods prior to use, as well as during transportation and processing of blood samples, readily form a stable partition under normal centrifugation conditions and be relatively inert or unreactive toward the substance(s) in the blood whose presence or concentration is to be determined.

Inertness to substances sought to be determined is a particular concern when blood collection vessels are used for therapeutic drug monitoring (TDM), which is assuming an increasingly important role in drug treatment strategies. TDM enables the administration of drugs in the appropriate therapeutic ranges, established through the accumulated experience of clinicians, and consequently reduces the number of patients receiving dosage levels that are either below detection limits or toxic. Administration of drugs under TDM allows one to take into account such factors as drug tolerance developed with passage of time, presence of multiple physical disorders and synergistic or antagonistic interactions with other therapeutic agents. Among the drugs recommended for administration under TDM are those having dangerous toxicity with poorly defined clinical endpoint, steep dose-response curve, narrow therapeutic range, considerable inter-individual pharmacokinetic variability or non-linear pharmacokinetics, as well as those used in long term therapy or in the treatment of life-threatening diseases. By way of example, the evaluation of blood levels of a number of tricyclic antidepressant compounds, such as imipramine or desipramine, in relation to an empirically established therapeutic range is reported to be particularly useful in the treatment of seemingly drug-refractive depression. TDM is likewise used to monitor the dosage of anticonvulsant drugs, such as phenytoin and phenobarbital which are administered in the treatment of epilepsy, antitumor drugs, such as methotrexate, and other more commonly prescribed drugs, including, but not limited to digoxin, lidocaine, pentobarbital and theophylline.

Reports of recent studies on the effect of blood partitioning compositions on drug concentrations in serum and plasma indicate that care must be taken in the selection of polymeric materials which come into contact with the blood samples obtained for drug assay. See, for example, P. Orsulak et al., *Therapeutic Drug Monitoring*, 6:444-48 (1984) and Y. Bergqvist et al. *Clin. Chem.*, 30:465-66 (1984). The results of these studies show that the blood partitioning compositions provided in blood collection vessels may account for reduced serum or plasma values, as a result of drug absorption by one or more components of the composition. The reported decreases in measured drug concentrations appears to be time-dependent. One report concludes that the observed decreases in drug concentrations may effectively be reduced by minimizing the interval between collection and processing. Another report recommends that blood samples be transported to the laboratory as soon as possible, with processing occurring within 4 hours. A commercially useful blood collection vessel, however, must produce accurate test results, taking into account routine clinical practices in large institutions, where collection, transportation and processing of blood samples may realistically take anywhere from about 1–72 hours.

British patent 685,649 teaches a process for the preparation of polyesters made by reacting succinic acid having an open chain hydrocarbon radical containing from 18 to 26 carbon atoms directly joined to at least one of the methylene groups and an organic compound having two esterifiable hydroxyl groups. There is no teaching of polyesters made by reacting other dicarboxylic acid components such as a second dicarboxylic acid having from 4 to about 12 carbon atoms and/or a third dicarboxylic acid component having from about 5 to about 25 mole percent of an aliphatic dicarboxylic acid having about 36 carbon atoms or that such polyesters are useful as functional blood partitioning compositions having reduced affinity for therapeutic agents present in blood such as phenobarbital and imipramine.

U.S. Pat. No. 4,148,764 teaches polyesters useful as a barrier material in blood separation assemblies. The polyesters are comprised of the reaction products of essentially stoichiometric quantities of: (1) a dicarboxylic acid component which is comprised of: (a) aliphatic dicarboxylic acid having from 4 to about 12 carbon atoms, (b) a polymeric fatty acid containing 75% by weight or more of a $C_{36}$ dibasic acid; (2) a diol component which includes a branched-chain aliphatic dihydric alcohol having 3 to 8 carbon atoms, a mixture of these dihydric alcohols, or a mixture containing at least 50% by weight of the branched-chain aliphatic dihydric alcohols and a straight-chain aliphatic dihydric alcohol having 2 to 8 carbon atoms. The equivalents ratio of (a) to (b) ranges from 0.80:0.20 to 0.97:0.03. The polyesters have an average molecular weight of 2,000–8,000, a kinematic viscosity at 210° F. of 2,000–8,000 centistokes, and a density in the range of from 1.015 to 1.060 g/cm$^3$. U.S. Pat. No. 4,148,764 does not teach that the dicarboxylic acid component contains a third dicarboxylic acid having from 13 to about 22 carbon atoms. The presence of the third dicarboxylic acid having from 13 to about 22 carbon atoms according to the invention produces a product which, when formulated together with other ingredients such as a suitable filler and compatible surfactant, is a functional blood partitioning composition which has reduced affinity for therapeutic agents present in blood such as phenobarbital and imipramine. U.S. Pat. No. 4,480,087 teaches polyester waxes which contain as the acid member at least 75 mole percent of alkylsuccinic anhydride or alkenylsuccinic anhydride and the acid functional derivatives thereof, and linear aliphatic and cycloaliphatic glycols having from 2 to 12 carbon atoms as the diol member. The remaining acid member may be a $C_4$ to $C_{10}$ dibasic aliphatic acid such as succinic or adipic acid. The patent does not teach polyester compositions having less than 75 mole percent of alkylsuccinic anhydride which is an aliphatic dicarboxylic acid having from 13 to about 22 carbon atoms nor does it contain any suggestion that such polyester compositions are useful as functional blood partitioning compositions having reduced affinity for therapeutic agents present in blood such as phenobarbital and imipramine.

SUMMARY OF THE INVENTION

In accordance with the present invention, it has been discovered that certain highly hydrophobic polyesters satisfy the above-noted criteria for incorporation in a clinically useful blood partitioning composition. The polyesters according to the invention comprise a dicarboxylic acid member and a diol member. The dicarboxylic acid member is comprised of three separate dicarboxylic acid components. The first acid component includes from about 5 to about 60 mole percent of an aliphatic dicarboxylic acid having from 13 to about 22 carbon atoms. The second contains from about 35 to about 90 mole percent of an aliphatic dicarboxylic acid having from 4 to about 12 carbon atoms. The third is comprised of from about 5 to about 25 mole percent of an aliphatic dicarboxylic acid having about 36 carbon atoms. The molar ratio of acid member to diol member is about 1:1. The polyester is in the form of a viscous liquid and having a density at room temperature in the range of 1.01–1.09.

The polyesters of the invention are readily formulated together with other ingredients, typically a suitable filler and compatible surfactant, into functional blood partitioning compositions. The density of the finished blood partitioning composition is controlled within prescribed limits, so that during centrifugation the composition becomes stably positioned at the interface between the serum or plasma phase and heavier cellular phase and, when centrifugation is terminated, forms a continuous integral barrier within the blood collection vessel to prevent the two phases from recombining or mixing, especially when decanting or pipetting the serum or plasma. The blood partitioning compositions of the invention are advantageously employed in small amounts, on the order of 1–5 gm., in a 10 ml blood collection vessel of the type previously described which are then ready for use in blood sampling and analysis in the usual way. The polyester-based blood partitioning compositions of the invention are especially suited for use in TDM procedures, displaying negligible interaction with commonly monitored therapeutic agents.

DESCRIPTION OF THE PREFERRED EMBODIMENTS

The polyesters according to the invention have molecular weights from about 3,000 to about 12,000 (number average, as determined by gel permeation chromatography). The polyesters of the invention are produced in the form of viscous liquids, having a density at room temperature in the range of 1.01–1.09. Particularly notable among the properties of these polyesters is their inertness, making them especially useful in TDM programs. The polyesters of the invention are also highly hydrophobic, exhibiting negligible water solubility. The physical and chemical properties of these polyesters are uniformly maintained over extended periods prior to use, as well as during transportation and processing of blood samples. Among the other notable characteristics of these polyesters is the ability to undergo ultracentrifugation for up to 1 hour at up to 1500G (G being the ratio of centrifugal acceleration to acceleration of gravity), without any detectable adverse effect.

The polyesters of the invention are further characterized by having an acid value of 2 or less, an hydroxyl value of 25 or less and a 210° F. kinematic viscosity of about 1700–4000 centistokes.

Polyesters having the above-described properties are especially useful as blood partitioning agents in blood collection vessels where they provide a continuous integral barrier or seal between the serum and clot portions of blood. In other words, the polyester completely partitions the separated phases so that the serum and cellular or clot portions are no longer in contact at any point, forming a unitary seal which firmly adheres to the inner surface of the blood collection vessel. By forming a continuous, integral barrier in this way, it is possible to easily remove the serum or plasma portion by decanting or pipetting, with the clot portion remaining undisturbed in the collection vessel.

The dicarboxylic acid member of the polyesters of the invention is comprised of three dicarboxylic acids, the first of which includes aliphatic dicarboxylic acids having from 13 to about 22 carbon atoms. The first dicarboxylic acid is preferably selected from the group of polyalkenylsuccinic acids such dodecenylsuccinic acid or dodecenylsuccinic anhydride, adducts of unsaturated monocarboxylic acids such as a linoleic acid-acrylic acid adduct, or a mixture thereof.

The second group of dicarboxylic acids includes saturated aliphatic acids having 4–12 carbon atoms. More preferably, these acids have from 4–9 carbon atoms and are essentially straight-chain acids. Representative short chain dicarboxylic acids include succinic acid, glutaric acid, adipic acid, pimelic acid, suberic acid, azelaic acid, sebacic acid, undecanedoic acid and dodecanedoic acid. Mixtures of two or more of such short-chain dicarboxylic acids may be used, if desired.

The third group of dicarboxylic acids includes aliphatic dicarboxylic acids having from about 32–40 carbon atoms obtained by the polymerization of olefinically unsaturated monocarboxylic acids having from 16–20 carbon atoms, such as palmitoleic acid, oleic acid, linoleic acid, linolenic acid and the like. Polymeric fatty acids and processes for their production are well known. See, for example, U.S. Pat. Nos. 2,793,219 and 2,955,121. Polymeric fatty acids particularly useful in the practice of this invention preferably will have as their principal component C-36 dimer acid. Such C-36 dicarboxylic acids are obtained by the dimerization of two moles of a C-18 unsaturated monocarboxylic acid, such as oleic acid or linoleic acid, or mixtures thereof, e.g., tall oil fatty acids. These products typically contain 75% by weight or more of C-36 dimer acid and have an acid value in the range of 180–215, saponification value in the range of 190–215 and neutral equivalent from 265–310. The dimer acids may be hydrogenated prior to use. To increase the C-36 dimer content and reduce the amount of by-product acids, including unreacted monobasic acid, trimer and higher polymer acids, the polymeric fatty acid may be molecularly distilled or otherwise fractionated.

The first group of dicarboxylic acid comprises from about 5 to about 60 mole percent of the total acid component of the polyester. The second dicarboxylic acid group comprises from about 35 to about 90 mole percent of the total acid component of the polyester. The third group comprises from about 5 to about 25 mole percent of the total acid component of the polyester.

It will be apparent to those skilled in the art that the various art-recognized equivalents of the aforementioned dicarboxylic acids, including anhydrides and lower alkyl esters thereof, may be employed in preparing the polyesters of the invention. Accordingly, as used herein, the term "acid" is intended to encompass such acid derivatives. Methyl esters are particularly advantageous for the preparation of the polyesters described herein. Mixtures of acids, anhydrides and esters may also be reacted to obtain the desired product.

Suitable diols which may be reacted with the above described dicarboxylic acid(s) to yield the polyesters of the invention include diols of the formula:

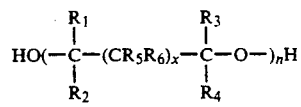

in which $R_1$, $R_2$, $R_3$ and $R_4$ are independently selected from the group consisting of hydrogen and an alkyl group having 1–4 carbon atoms, $n=1-4$ and $x=0-4$. Representative diols falling within the foregoing formula include neopentyl glycol, propylene glycol, diethylene glycol, triethylene glycol, 3-methyl-1,5-pentane diol, 1,2 propane diol, 1,3-butane diol, 1,2-butane diol, 1,2-pentane diol, 1,3-pentane diol, 1,4-pentane diol and the like. The preferred diols contain from 3–5 carbon atoms, with particularly useful polyesters products being obtained using neopentyl glycol, propylene glycol, triethylene glycol, or mixtures thereof. In a particularly preferred embodiment of the invention, in which a mixture of neopentyl glycol and propylene glycol is used, the amount of neopentyl glycol comprises about 70 to about 95 equivalent percent, and the amount of propylene glycol comprises about 5 to about 30 equivalent percent of the total diol component equivalents.

Conventional esterification procedures and equipment are used to obtain the polyester of the invention. The reactive components are normally added to the reaction vessel as a unit charge and the reaction mixture is then heated with agitation at a temperature from about 150°–250° C. for a period of time sufficient to substantially complete the esterification reaction. The reaction may be driven to completion by application of vacuum (typically 1–5 mm Hg absolute at 200°–250° C.) until the desired properties are obtained. Vacuum distillation removes the final traces of water, any excess reactants and small amounts of other volatile materials present in the reaction mixture.

If an improvement in color is desired, the polyester may be bleached by any of the well known and acceptable bleaching methods, e.g., using hydrogen peroxide or chlorite. Alternatively, the polyester may be decolorized by filtering through a filter aid, charcoal or bleaching clay.

The rate of esterification may be enhanced by the use of known esterification catalysts. Suitable esterification catalysts for enhancing the rate of esterification of free carboxyl groups include phosphoric acid, sulfuric acid, toluenesulfonic acid, methane sulfonic acid, and the like. The amount of such catalyst may vary widely, but most often will be in an amount from about 0.1% to about 0.5% by weight, based on the total reactant charge. Catalysts useful for effecting ester interchange include dibutyltin diacetate, stannous oxalate, dibutyltin oxide, tetrabutyl titanate, zinc acetate and the like. These catalysts are generally employed in an amount ranging from about 0.01% to 0.05% by weight, based on the total resistant charge. When such catalysts are used, it is not necessary that it be present throughout the entire reaction. It is sometimes advantageous in order to obtain products having good color and relatively low acid value, on the order of 2 mg KOH/gm, or less, to add the catalyst during the final stages of the reaction. Upon completion of the reaction, the catalyst may be deactivated and removed by filtering or other conventional means.

Inert diluents, such as benzene, toluene, xylene and the like may be employed for the reaction, however, the use of diluents is not necessary. It is generally considered desirable to conduct the reaction without diluents since the resultant polyester can be directly used as it is obtained from the reaction vessel. A small excess (based on the equivalents of acid present) of the diol component may be used if desired. The excess diol serves as the reaction medium and reduces the viscosity of the reaction mixture. The excess diol is distilled off as the esterification is carried to completion and may be recycled to the reactor if desired. Generally, about 20% by weight excess diol, based on the total weight of the diol component, will suffice. The more volatile glycols are commonly used for this purpose.

A particularly useful blood partitioning agent is obtained by reacting a total of 1.0 mole of acid member which comprised of: (i) about 10 mole percent of linoleic acid-acrylic acid adduct having 21 carbon atoms as the first acid component, (ii) about 75 mole percent of a mixture of dimethyl succinate, dimethyl glutarate, and dimethyl adipate as the second acid component, and (iii) about 15 mole percent of oleic dimer acid as the third acid component with about 1.0 moles of diol member comprising neopentyl glycol and propylene glycol. The relative approximate weight percentages of the esters in the ester mixture being 1% dimethyl succinate, 75% dimethyl glutarate and 24% dimethyl adipate. The equivalents ratio of neopentyl glycol to propylene glycol ranges from about 0.75:0.25 to about 0.90:0.10.

The source of the acids or acid derivatives and the manner by which the dicarboxylic acid blends are prepared, in those embodiments where such blends are used, is of no consequence so long as the resulting blend contains the specified acids or acid derivatives in the required ratios. Thus, dicarboxylic acid or acid derivative blends may be obtained by mixing the individual acid components. On the other hand, mixtures of acid obtained as by-products from various manufacturing operations and which contain one or more of the necessary acid components may be advantageously utilized. For example, mixed dimethyl esters of succinic, glutaric and adipic acids may be obtained as a co-product from the manufacture of adipic acid and may be conveniently blended with any other acid, e.g., oleic dimer acid selected for inclusion in the polyester of the invention.

Preparation of blood partitioning compositions using the polyesters of the invention may be carried out in the manner described in commonly owned U.S. Pat. Nos. 4,101,422 and 4,148,764, the entire disclosures of which are incorporated by reference in the present specification, as if set forth herein in full.

Determination of the extent of interaction between the polyesters of the invention and commonly monitored drugs may be carried out using well known recovery experiments and drug measurement techniques, such as, gas chromatography, gas-liquid chromatography, high-performance liquid chromatography, thin layer chromatography or immunoassay techniques, including radioimmunoassay, enzyme immunoassay, fluorescence polarization immunoassay, nephelometric assay, and the like. A variety of suitable procedures are reported in the literature. See, for example, Bergqvist et al., supra. Such determinations may be carried out using human serum, or commercially available bovine serum, if desired.

The following examples are presented to illustrate the invention more fully, and are not intended, nor are they to be construed, as a limitation of the scope of the invention. In the examples, all percentages are on a weight basis unless otherwise indicated.

EXAMPLE 1

A reactant charge was prepared, including 558 gm. of dodecenylsuccinic anhydride and 192 gm. of propylene glycol (which includes a 20% excess over the stoichiometric requirement for the reaction, to serve as the reaction medium), placed in a one liter reaction vessel equipped with a stirrer, fused and heated gradually to a final temperature of 225°-230° C. Water of reaction was collected from a temperature of approximately 190° C. The diol component was retained in the reaction mixture by the action of a Vigreaux fractionating column. The rate of temperature increase was regulated so that the still head temperature did not exceed 110° C. during the initial condensation. When the rate of water evolution diminished sharply, i.e., when about 85% of the expected distillate had been collected, a partial vacuum was applied to complete the conversion of acid groups present to esters (about 28 inches vacuum at 225° C.). The vacuum esterification stage required about 3-4 hours. At this point, an interchange catalyst was introduced (0.02% dibutyltin diacetate (DBTDA) based on the total reactant charge), the fractionating column was removed, and relatively high vacuum applied (approximately 1-2 mm Hg). Distillation of volatile diol proceeded slowly until the target viscosity was achieved, which required approximately 6 hours. The product was filtered through a coarse screen. The polyester recovered had an acid value of 3.0, an hydroxyl value of 22.4, 210° F. kinematic viscosity of 1978.

EXAMPLE 2

The same general procedure described in Example 1 was followed in preparing a polyester from a reactant charge comprising 314 gm. of dodecenylsuccinic anhydride, 221 gm. of azelaic acid and 215 gm. of propylene glycol, except that one half the amount of the DBTDA catalyst was used and vacuum distillation proceeded for an additional 2 hours. The resultant product had an acid value of 1.8, a hydroxyl value of 9.5, 210° F. kinematic viscosity of 2554.

EXAMPLE 3

A polyester was prepared from a reactant charge comprising 335 gm. linoleic acid-acrylic acid adduct, 661 gm. azelaic acid, 405 gm. neopentyl glycol and 99 gm. propylene glycol. The reaction was carried out in a 2 liter reaction vessel equipped with a stirrer and a Vigreaux fractionating column, following the same general reaction conditions set forth in Example 1, above, except that vacuum distillation was performed for approximately 10 hrs. overall. The polyester obtained from this reaction had an acid value of 0.73, an hydroxyl value of 18.6, 210° F. kinematic viscosity of 1912 and density at room temperature of 1.0348.

EXAMPLE 4

A polyester was prepared from a reactant charge including 229 gm. linoleic acid-acrylic acid adduct, 393 gm. of a mixture of dicarboxylic acid dimethyl esters, including 75% dimethyl glutarate, 24% dimethyl adipate and 1% dimethyl succinate, 390 gm. oleic dimer acid, 352 gm. neopentyl glycol and 86 gm. propylene glycol. The reaction was run in a 2 liter reaction vessel equipped as described in Example 3. The reaction conditions described in Example 1 were followed for the most part with certain variations. Specifically, the catalyst (DBTDA) was introduced at the outset of the reaction, and in an amount of 0.02%, based on the total weight of the reactant charge. In addition, the heating rate was adjusted so that the head temperature did not exceed 90° C. until an amount of distillate corresponding approximately to the predicted weight of methanol was collected. The upper limit of the reaction temperature was approximately 225° C. Stripping of the reaction medium to the desired viscosity was carried out essentially as described in Example 1, above. The polyester obtained from the reaction had an acid value of 1.1, an hydroxyl value of 14.1, 210° F. kinematic viscosity of 1972 and density at room temperature of 1.0202.

EXAMPLE 5

A reactant charge was prepared including 508 gm. dodecenylsuccinic anhydride 1116 gm. oleic acid dimer, 1123 gm. of the ester mixture described in Example 4, 1008 gm. neopentyl glycol and 245 gm. propylene glycol. This charge, together with 0.02% of DBTDA, was placed in a 5 liter reaction vessel equipped as described in Example 3, and reacted following the general procedure of Example 4. The reaction yielded a polyester having an acid value of 0.3, an hydroxyl value of 14.1, 210° F. kinematic viscosity of 2510 and density at room temperature of 1.0226.

EXAMPLE 6

A polyester was prepared from a reactant charge, including 196 gm. linoleic acid-acrylic acid adduct, 193 gm. dimethyl azelate, 558 gm. of the ester mixture described in Example 4, 445 gm. neopentyl glycol and 108 gm. propylene glycol, together with 0.02% DBTDA, following the general procedure of Example 4, with the exception that the usual vacuum esterification stage to reduce free acidity proved unnecessary in this case. The product of the reaction had an acid value of 0.4, an hydroxyl value of 8.3, 210° F. kinematic viscosity of 2256 and density at room temperature of 1.082.

EXAMPLE 7

To a 2 liter vessel was charged 735 grams of Emerox TM 1110 azelaic acid, 259 grams of Empol TM 1016 dimer acid, 101 grams of 1,2-propylene glycol, and 405 grams of neopentyl glycol. The reaction was carried out in the same manner as described in Example 1 including the addition of 0.02% di-n-butyltin diacetate when the evolution of water was complete. The resulting polyester exhibited an acid value of 1.1, a hydroxyl value of 14.8, a kinematic viscosity of 3370 cst @210° F., and a density of 1.0232@25° C.

EXAMPLE 8

To a 2 liter vessel was charged 585 grams of Emerox TM 1110 azelaic acid, 238 grams of Empol TM 1016 dimer acid, 174 grams of dodecenylsuccinic anhydride, 96 grams of 1,2-propylene glycol, and 394 grams of neopentyl glycol. The reaction was carried out in the same manner as described in Example 1 including the addition of 0.02% di-n-butyltin diacetate when the evolution of water was complete. The resulting polyester exhibited an acid value of 0.80, a hydroxyl value of 24.5, a kinematic viscosity of 2132 cst @210° F., and a density of 1.0196@25° C.

Polyesters prepared as described in the foregoing examples were evaluated for interaction with the antidepressant, imipramine (IM) and the anticonvulsant, phenobarbital (PB), two drugs which are commonly administered under TDM. A recovery of 90% was established as a benchmark for utilization of the polyesters of the invention in TDM programs. The results of these evaluations are set forth below in Table I. The entries under the headings IM and PB are the percent recoveries of imipramine and phenobarbital respectively.

TABLE I

|      | $C_{4-12}$ | $C_{13-22}$ | $C_{36}$ | DIOL | IM | PB |
|------|-----------|-------------|----------|------|-----|-----|
| Ex 1 | —         | 1.0         | —        | 1.0  | 93  | 97  |
| Ex 2 | 0.5       | 0.5         | —        | 1.0  | 89  | 96  |
| Ex 3 | 0.812     | 0.188       | —        | 1.0  | 88  | 95  |
| Ex 4 | 0.90      | 0.10        | —        | 1.0  | 97  | 99  |
| Ex 5 | 0.64      | 0.18        | 0.18     | 1.0  | 86  | 100 |
| Ex 6 | 0.90      | 0.10        | —        | 1.0  | 89  | 92  |
| Ex 7[1] | 0.884  | —           | 0.116    | 1.0  | 77  | 95  |
| Ex 8 | 0.748     | 0.098       | 0.154    | 1.0  | 87  | 97  |

1-a polyester according to U.S. Pat. No. 4,148,764 All of the recovery values reported above were obtained using commercially available bovine serum. Experience has shown that higher recovery values (up to about 2% higher) are obtainable with human serum.

The data in Table I show that a substantial improvement in the ability to determine the level of imipramine in bovine sera by recovery of radioactive content, expressed as a percentage of the dose introduced, was achieved when at least half of the $C_{36}$ dimer acid content of the polyesters taught in U.S. Pat. No. 4,184,764 was replaced by acid, ester, or anhydride having from 13 to 22 carbon atoms with a relatively large pendant alkyl group having from about 9 to about 13 carbon atoms.

While the present invention has been described and exemplified above in terms of certain preferred embodiments, various other embodiments may be apparent to those skilled in the art. Accordingly, the invention is not limited to the embodiments specifically described and exemplified, but variations and modifications may be made therein and thereto without departing from the spirit of the invention, the full scope of which is delineated by the following claims.

What is claimed is:

1. A polyester comprising about one mole of a dicarboxylic acid member and one mole of a diol member wherein said acid member is comprised of a first dicarboxylic acid component having from about 5 to about 60 mole percent of an aliphatic dicarboxylic acid having from 13 to about 22 carbon atoms, a second dicarboxylic acid component having from about 35 to about 90 mole percent of an aliphatic dicarboxylic acid having from 4 to about 12 carbon atoms, a third dicarboxylic acid component having from about 5 to about 25 mole percent of an aliphatic dicarboxylic acid having about 36 carbon atoms, said polyester being in the form of a viscous liquid and having a density at room temperature in the range of 1.01–1.09.

2. A polyester in accordance with claim 1, wherein said first dicarboxylic acid component is selected from the group consisting of a polyalkenylsuccinic acid, an adduct of unsaturated monocarboxylic acids, or a mixture thereof.

3. A polyester in accordance with claim 1, wherein said diol has the general formula

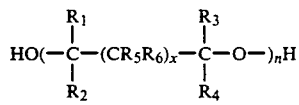

in which R1, R2, R3, R4, R5 and R6 are independently selected from the group consisting of hydrogen and alkyl having 1–4 carbon atoms, n=1–4 and x=0–4.

4. A polyester in accordance with claim 2, wherein said diol is selected from the group consisting of propylene glycol, neopentyl glycol, triethylene glycol or a mixture thereof.

5. A polyester in accordance with claim 2, wherein said second dicarboxylic component acid is selected from the group consisting of succinic acid, glutaric acid, adipic acid, pimelic acid, suberic acid, azelaic acid, sebacic acid, undecanedioic acid, dodecanedioic acid, oleic dimer acid, or mixtures thereof.

6. A polyester in accordance with claim 2, wherein said third dicarboxylic acid component is a $C_{36}$ dimer acid.

7. A polyester in accordance with claim 1 having an acid value of 2 or less, an hydroxyl value of 25 or less and a 210° F. kinematic viscosity of about 1700–4000 centistokes.

8. A polyester which comprises as the acid member: (i) about 10 mole percent of linoleic acid-acrylic acid adduct having 21 carbon atoms as the first acid component, (ii) about 75 mole percent of a mixture of dimethyl succinate, dimethyl glutarate, and dimethyl adipate as the second acid component, and (iii) about 15 mole percent of oleic dimer acid as the third acid component and a diol member comprising neopentyl glycol and propylene glycol wherein the molar ratio of said acid member to said diol member is about 1:1.

9. A polyester in accordance with claim 8 wherein said second acid component is comprised of about 1% by weight dimethyl succinate, 75% about by weight dimethyl glutarate and about 24% by weight dimethyl adipate.

10. A polyester in accordance with claim 8 wherein said diol member is comprised of neopentyl glycol and propylene glycol in an equivalents ratio of from about 0.75:0.25 to about 0.90:0.10.

* * * * *